United States Patent
Jang et al.

(10) Patent No.: US 11,774,439 B2
(45) Date of Patent: Oct. 3, 2023

(54) INTEGRATED BIOCHEMICAL SENSOR AND METHOD OF MANUFACTURING THE SAME

(71) Applicant: DAEGU GYEONGBUK INSTITUTE OF SCIENCE AND TECHNOLOGY, Daegu (KR)

(72) Inventors: Kyung In Jang, Seoul (KR); Jun Woo Yea, Daegu (KR); Han Hee Jung, Daegu (KR)

(73) Assignee: DAEGU GYEONGBUK INSTITUTE OF SCIENCE AND TECHNOLOGY, Daegu (KR)

(*) Notice: Subject to any disclaimer, the term of this patent is extended or adjusted under 35 U.S.C. 154(b) by 0 days.

(21) Appl. No.: 17/212,248

(22) Filed: Mar. 25, 2021

(65) Prior Publication Data
US 2022/0178908 A1 Jun. 9, 2022

(30) Foreign Application Priority Data
Dec. 9, 2020 (KR) .................. 10-2020-0171389

(51) Int. Cl.
*G01N 33/487* (2006.01)
*G01N 27/327* (2006.01)
*G01N 27/416* (2006.01)
*G01N 27/403* (2006.01)

(52) U.S. Cl.
CPC ..... *G01N 33/48728* (2013.01); *G01N 27/327* (2013.01); *G01N 27/403* (2013.01); *G01N 27/4163* (2013.01)

(58) Field of Classification Search
CPC .... G01N 27/327; G01N 27/27; G01N 27/333; G01N 27/3335; G01N 33/0001; G01N 27/403; G01N 27/4163; G01N 33/48728
See application file for complete search history.

(56) References Cited

U.S. PATENT DOCUMENTS

| 4,661,235 A | * | 4/1987 | Krull | ............ G01N 27/3335 204/403.08 |
| 5,789,250 A | * | 8/1998 | Ikezaki | ............ G01N 33/02 436/24 |
| 7,858,036 B2 | * | 12/2010 | Kugimiya | ............ G01N 27/327 422/50 |

FOREIGN PATENT DOCUMENTS

| CN | 109991282 A | | 7/2019 |
| JP | 2012083314 A | * | 4/2012 |
| JP | 2020-56750 A | | 4/2020 |
| KR | 20200038022 A | | 4/2020 |
| KR | 10-2020-0117013 A | | 10/2020 |

(Continued)

OTHER PUBLICATIONS

Winquist, F., Krantz-Rülcker, C. and Lundström, I., Electronic Tongues and Combinations of Artificial Senses. Sensors Update, 2002, 11: 279-306. (Year: 2002).*

(Continued)

*Primary Examiner* — Joshua L Allen
*Assistant Examiner* — Shizhi Qian
(74) *Attorney, Agent, or Firm* — Harness, Dickey & Pierce, P.L.C.

(57) ABSTRACT

Disclosed is an integrated biochemical sensor including a reference electrode, a plurality of working electrodes each having different artificial lipid membranes, and partition layers for electrically insulating the reference electrode and each of the working electrodes.

14 Claims, 16 Drawing Sheets

(56) References Cited

FOREIGN PATENT DOCUMENTS

WO    WO-2007096849 A1 *  8/2007  ............. G01N 27/48

OTHER PUBLICATIONS

Tahara Y, Nakashi K, Ji K, Ikeda A, Toko K. Development of a portable taste sensor with a lipid/polymer membrane. Sensors (Basel). Jan. 16, 2013;13(1):1076-84. (Year: 2013).*
Sim, M.Y.M.; Shya, T.J.; Ahmad, M.N.; Shakaff, A.Y.M.; Othman, A.R.; Hitam, M.S. Monitoring of Milk Quality With Disposable Taste Sensor. Sensors 2003, 3, 340-349. (Year: 2003).*
Tahara Y, Ikeda A, Maehara Y, Habara M, Toko K. Development and evaluation of a miniaturized taste sensor chip. Sensors (Basel). 2011;11(10):9878-9886. (Year: 2011).*
Mahato, Manmatha, et al. "Poly (N-[4H-1,2,4-triazol-4-yl] acrylamide) with different ratio of poly (vinyl chloride) composite membrane for liquid phase sensing of alcohol." Journal of Applied Polymer Science 134, pp. 1-15 (2017) (Year: 2017).*
Baret, M., et al. "Halide ion-selective electrode array calibration." Taianta 50.3, p. 541-558 (1999) (Year: 1999).*
Korean Office Action dated Dec. 9, 2022 issued in Korean Patent Application No. 10-2020-0171389.
Sharma, et al. "Development of Lipid Membrane based Taste Sensors for Electronic Tongue," Procedia Computer Science, vol. 70, pp. 146-152 (2015).
Korean Notice of Allowance dated May 23, 2023 issued in Korean Patent Application No. 10-2020-0171389.

* cited by examiner

INTEGRATED BIOCHEMICAL SENSOR AND METHOD OF MANUFACTURING THE SAME

CROSS-REFERENCE TO RELATED APPLICATION

This application claims priority to Korean Patent Application No. 10-2020-0171389, filed on Dec. 9, 2020 in the Korean Intellectual Property Office, the disclosure of which is incorporated herein by reference.

BACKGROUND OF THE DISCLOSURE

Field of the Disclosure

The present disclosure relates to an integrated biochemical sensor and a method of manufacturing the same, and more particularly, to a technical idea of detecting a plurality of biochemical substances using a single sensor.

Description of the Related Art

In general, a biochemical sensor refers to a hybrid device made in the form of a semiconductor chip by combining a semiconductor with various chemical substances, biochemical substances, or biological substances such as enzymes, proteins, antibodies, and DNA. A typical example of the biochemical sensor is a taste sensor for detecting at least one of sweetness, bitterness, sourness, saltiness, astringency, and savory taste.

Conventional biochemical sensors are excellent in terms of reliability, but the conventional biochemical sensors are difficult to use in various environments because devices for detecting and converting information on biochemical substances and accompanying equipment are very large and heavy, and operate in a wired manner.

RELATED ART DOCUMENTS

Patent Documents

Korean Patent Application Publication No. 10-2020-0038022, "TASTE BIOSENSOR INCLUDING GUSTATORY CELLS AND NERVE CELLS"

SUMMARY OF THE DISCLOSURE

Therefore, the present disclosure has been made in view of the above problems, and it is an object of the present disclosure to provide an integrated biochemical sensor capable of simultaneously detecting a plurality of biochemical substances using a reference electrode and a plurality of working electrodes having different types of artificial lipid membranes and a method of manufacturing the integrated biochemical sensor.

It is another object of the present disclosure to provide an integrated biochemical sensor and a method of manufacturing the same. In the integrated biochemical sensor, a plurality of working electrodes is designed to have a laminated structure consisting of a stabilizing layer, an electrolyte layer, and an artificial lipid membrane. Thus, in detecting a signal corresponding to a biochemical substance, reliability and stability may be increased, and sustainability for sensing operation may be secured.

In accordance with one aspect of the present disclosure, provided is an integrated biochemical sensor including a reference electrode; a plurality of working electrodes each having different artificial lipid membranes; and partition layers for electrically insulating the reference electrode and each of the working electrodes.

According to one aspect, membrane potentials of the artificial lipid membranes may change due to chemical reaction with biochemical ions corresponding to the artificial lipid membranes.

According to one aspect, the biochemical ions may be detected based on a potential difference between the reference electrode and a working electrode having the artificial lipid membrane, a membrane potential of which is changed, among the working electrodes.

According to one aspect, each of the working electrodes may further include a working electrode layer, a stabilizing layer, and an electrolyte layer for improving electrical connectivity between the working electrode layer and the artificial lipid membrane.

According to one aspect, the stabilizing layer may include at least one of silver (Ag), silver chloride (AgCl), and polyvinyl butyral (PVB).

According to one aspect, the electrolyte layer may include at least one of poly(2-hydroxyethyl methacrylate) (pHEMA) and PEDOT:PSS.

According to one aspect, the partition layers may include a lower encapsulation layer for protecting the working electrodes from external impact, an insulating encapsulation layer for electrically insulating each of the working electrodes and the reference electrode, and an upper encapsulation layer for protecting the reference electrode from external impact.

According to one aspect, the working electrodes may include a first working electrode for detecting biochemical ions corresponding to saltiness through a first artificial lipid membrane, a second working electrode for detecting biochemical ions corresponding to bitterness through a second artificial lipid membrane, a third working electrode for detecting biochemical ions corresponding to sweetness through a third artificial lipid membrane, and a fourth working electrode for detecting biochemical ions corresponding to sourness through a fourth artificial lipid membrane.

According to one aspect, the first artificial lipid membrane may include at least one of tetradodecylammonium, bromide 1-hexadecanol, and di-n-octyl phenylphosphonate.

According to one aspect, the second artificial lipid membrane may include at least one of methyl trioctyl ammonium chloride and di-n-octyl phenylphosphonate.

According to one aspect, the third artificial lipid membrane may include at least one of tetradodecylammonium bromide and di-n-octyl phenylphosphonate.

According to one aspect, the fourth artificial lipid membrane may include at least one of methyl trioctyl ammonium chloride, oleic acid, bis(2-ethylhexyl) phosphate, and dioctyl phenyl phosphonate.

In accordance with another aspect of the present disclosure, provided is a method of manufacturing an integrated biochemical sensor, the method including forming a plurality of working electrode layers; forming an insulating encapsulation layer for electrically insulating each of the working electrode layers and a reference electrode layer; forming the reference electrode layer on the insulating encapsulation layer; forming an upper encapsulation layer for protecting the reference electrode layer from external impact on the insulating encapsulation layer; and forming artificial lipid membranes on the working electrode layers.

According to one aspect, the forming of the artificial lipid membranes may further include forming a stabilizing layer on the working electrode layers and the reference electrode layer; forming an electrolyte layer on the working electrode layers on which the stabilizing layer has been formed and the reference electrode layer on which the stabilizing layer has been formed; and forming the artificial lipid membranes on the working electrode layers on which the electrolyte layer has been formed.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Figure 1:
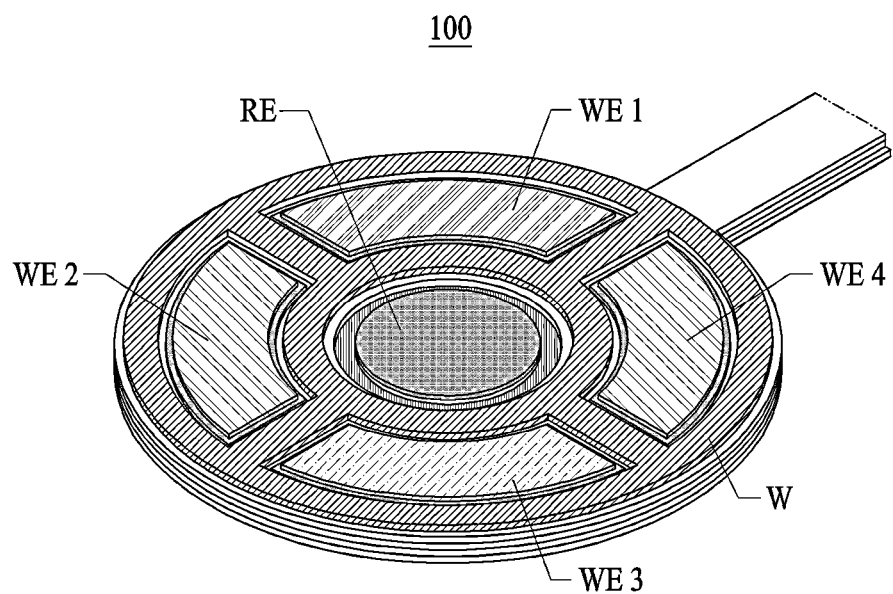
FIG. 1 illustrates an integrated biochemical sensor according to one embodiment.
Figure 2A:
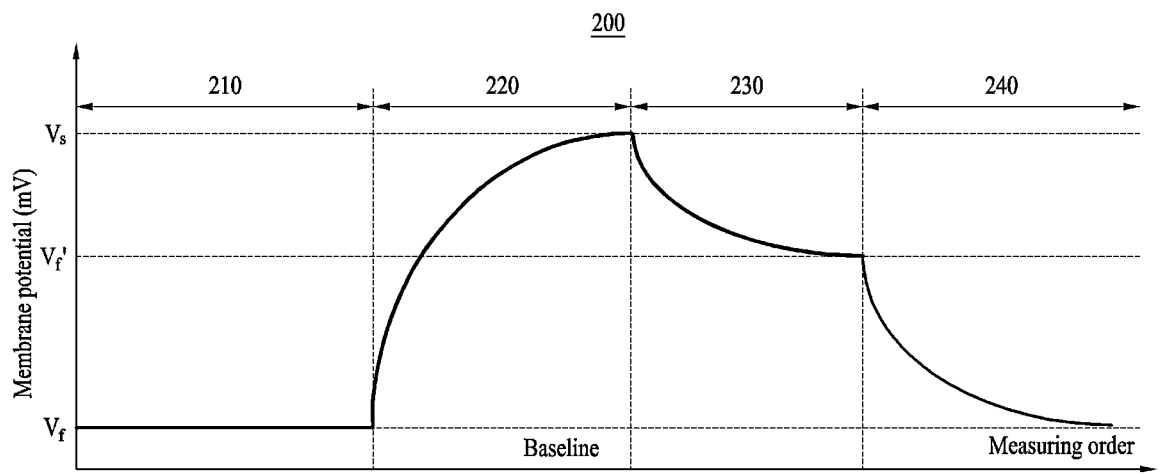
FIGS. 2A to 2E are diagrams for explaining the process of detecting biochemical ions using an integrated biochemical sensor according to one embodiment.
Figure 2B:
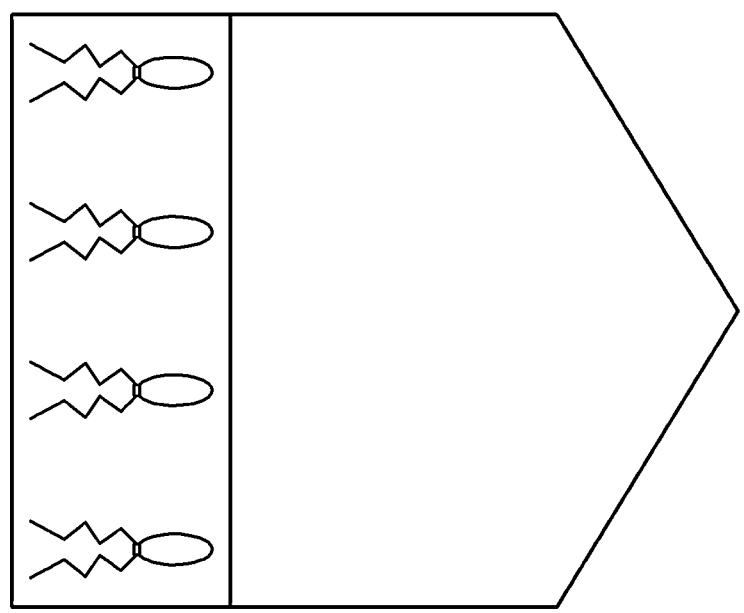
Figure 2C:
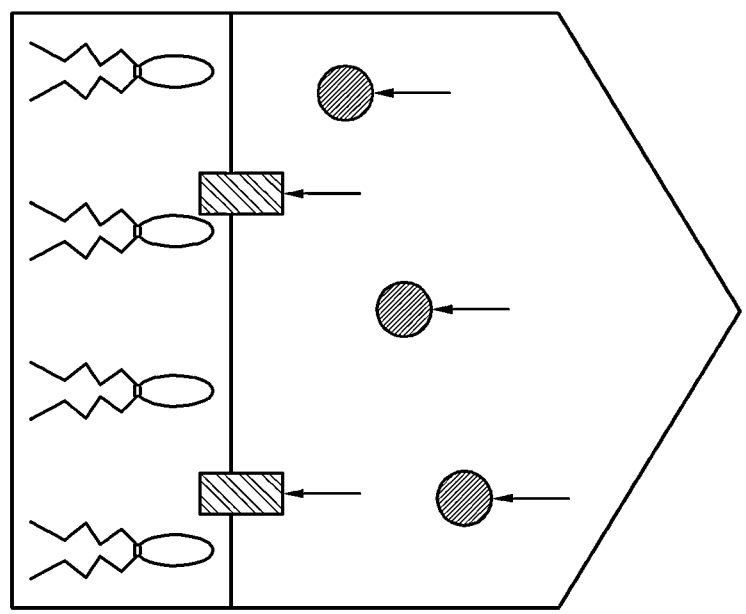
Figure 2D:
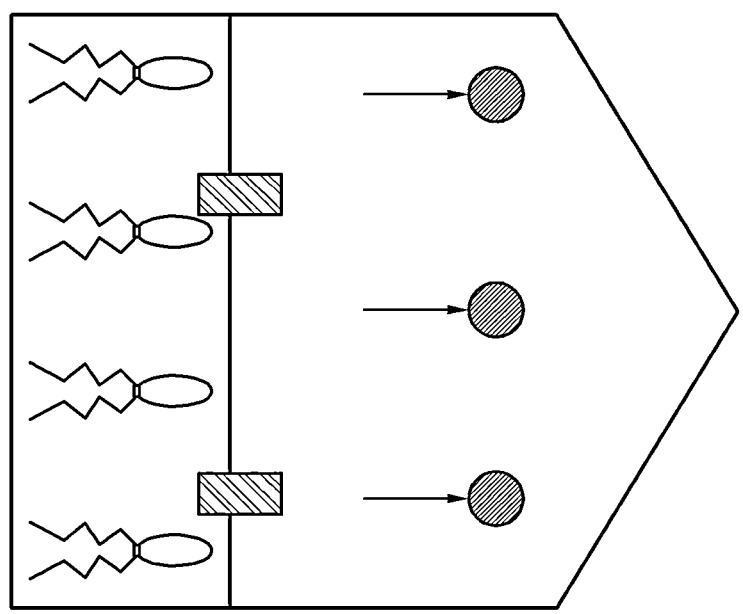
Figure 2E:
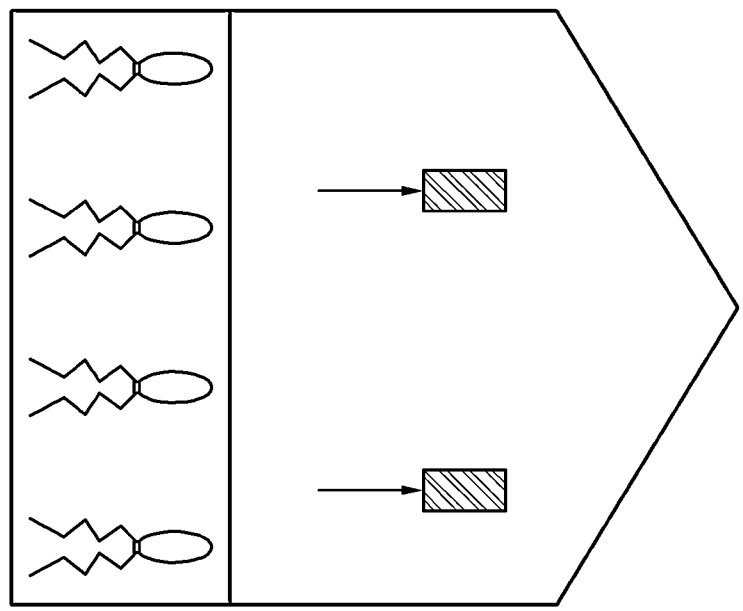
Figure 3A:
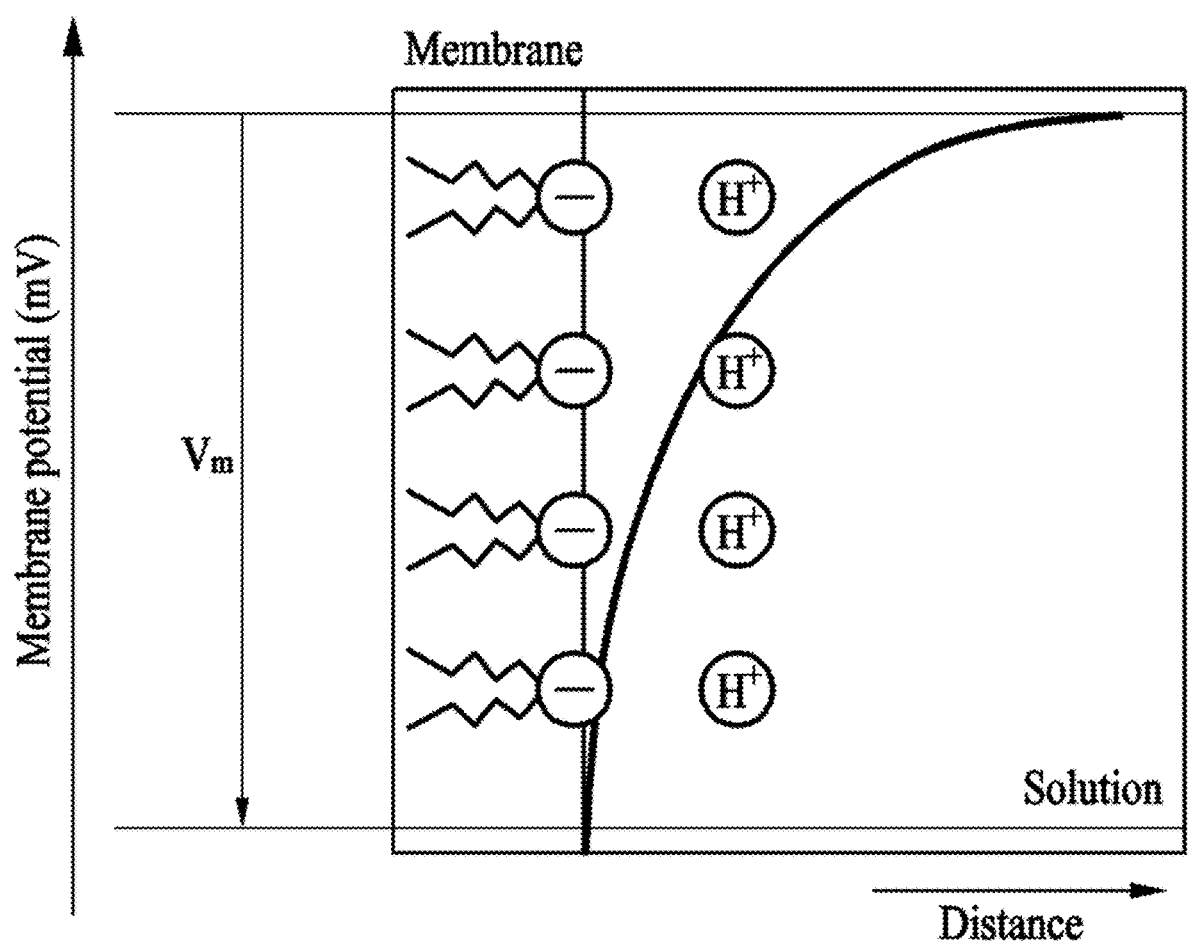
FIGS. 3A to 3G are diagrams for explaining examples of detecting biochemical ions corresponding to sourness and bitterness using an integrated biochemical sensor according to one embodiment.
Figure 3B:
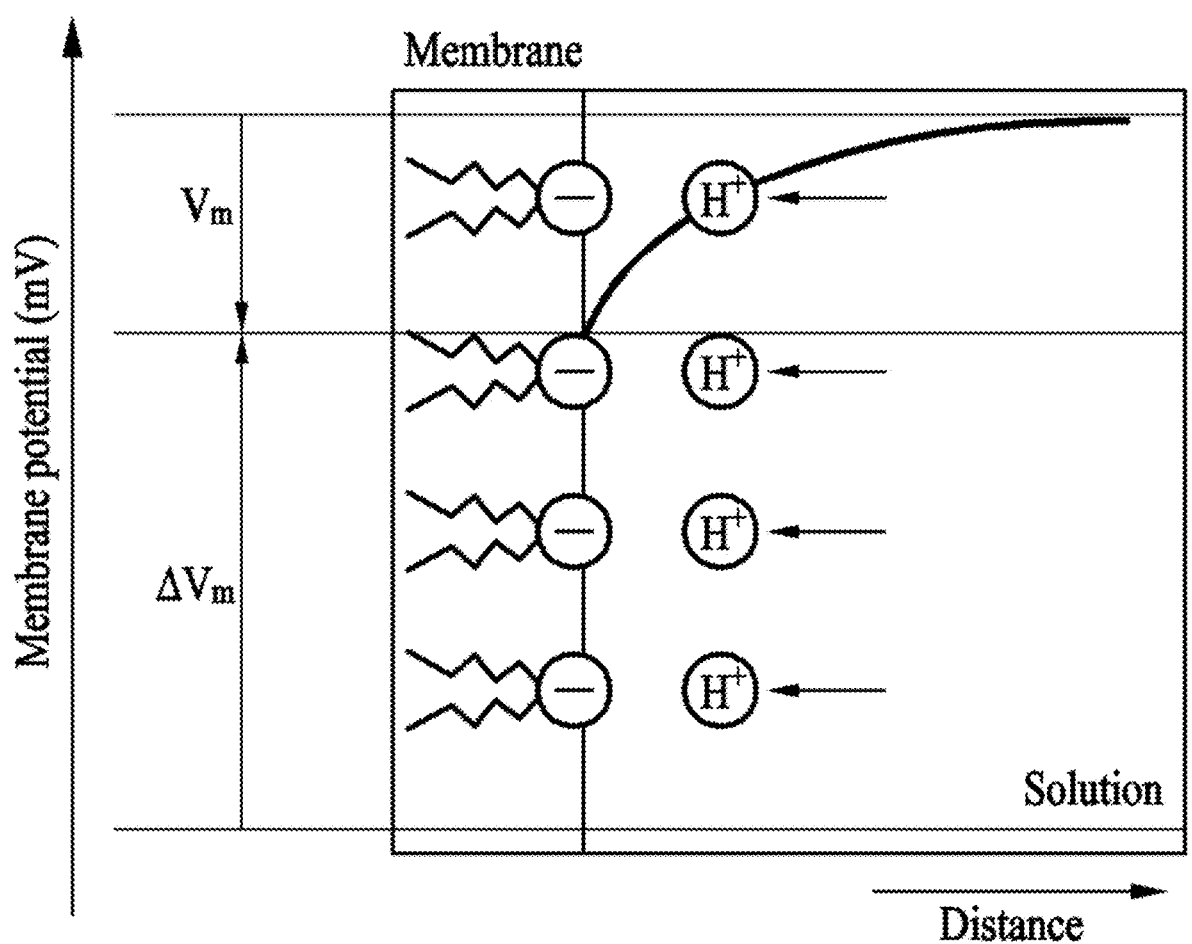
Figure 3C:
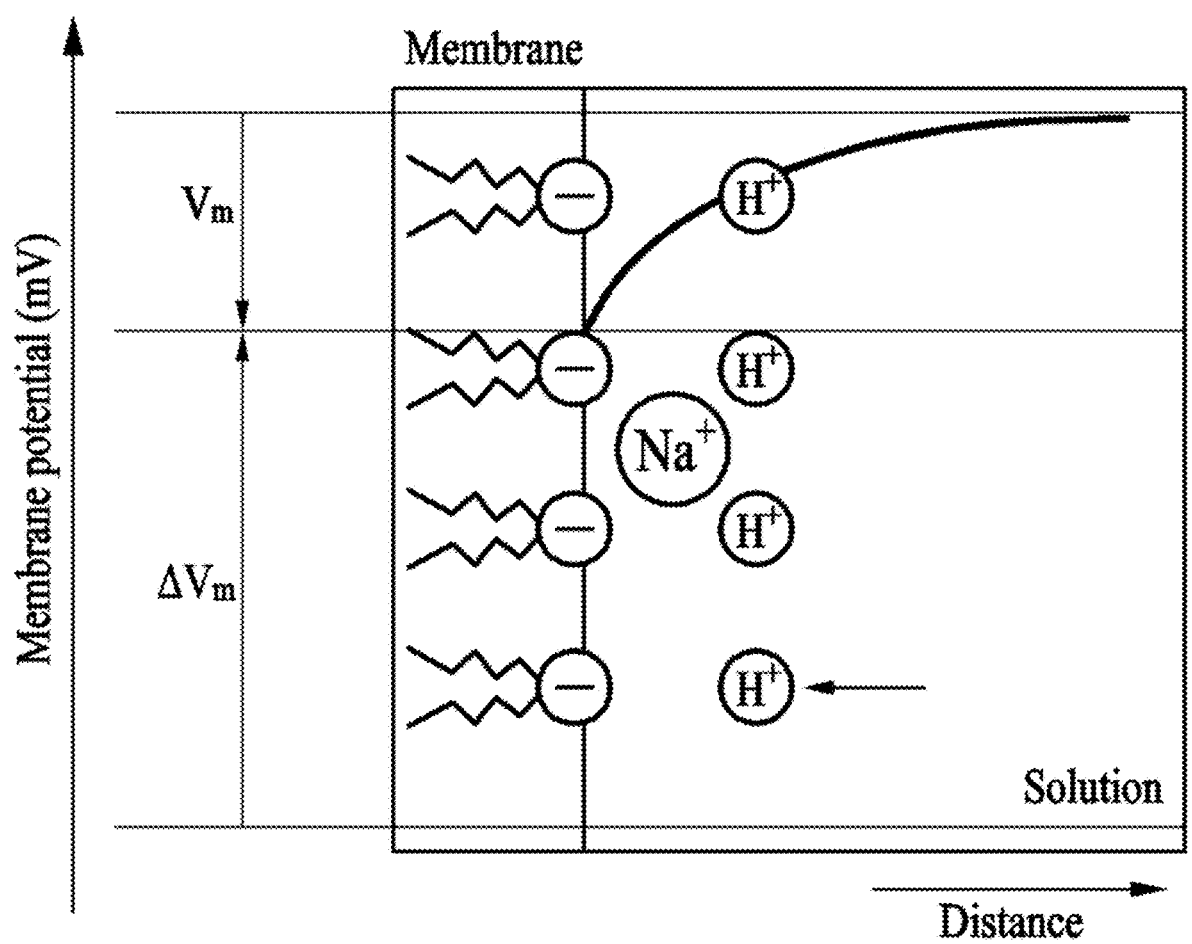
Figure 3D:
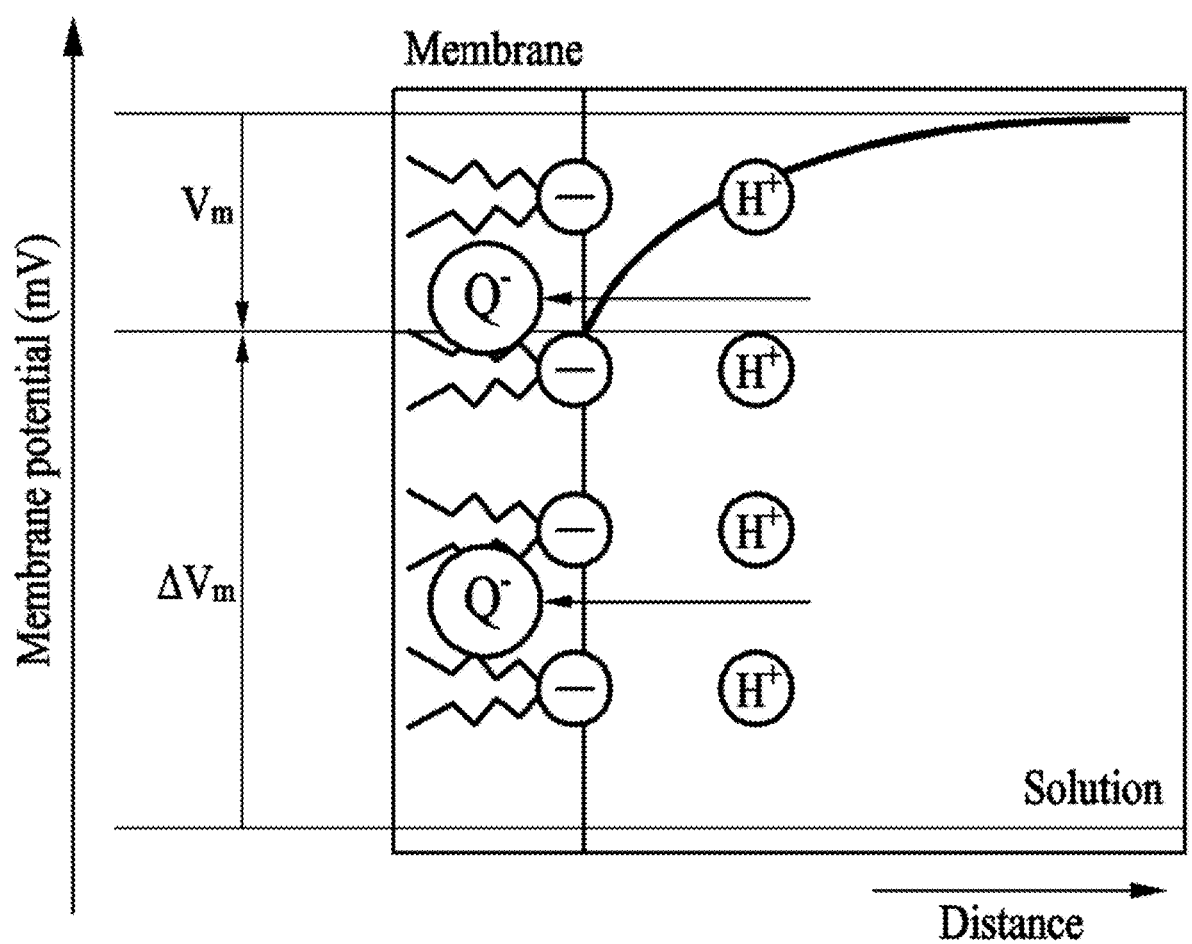
Figure 3E:
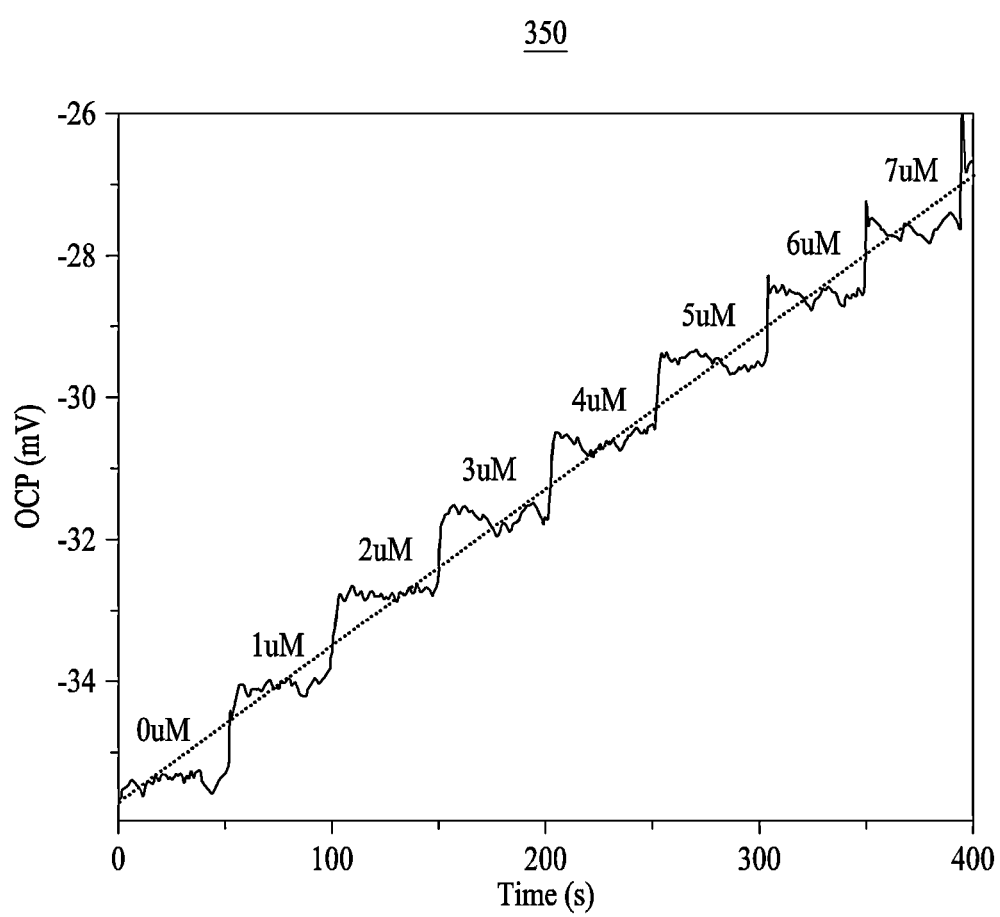
Figure 3F:
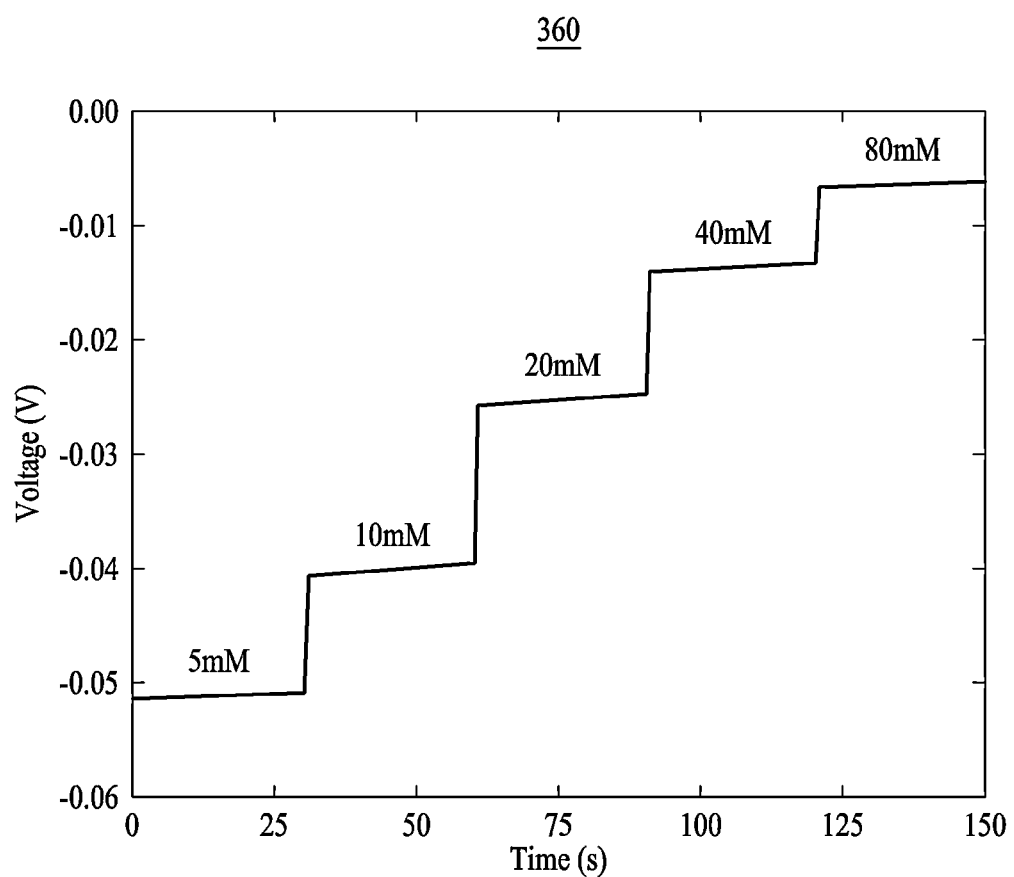
Figure 3G:
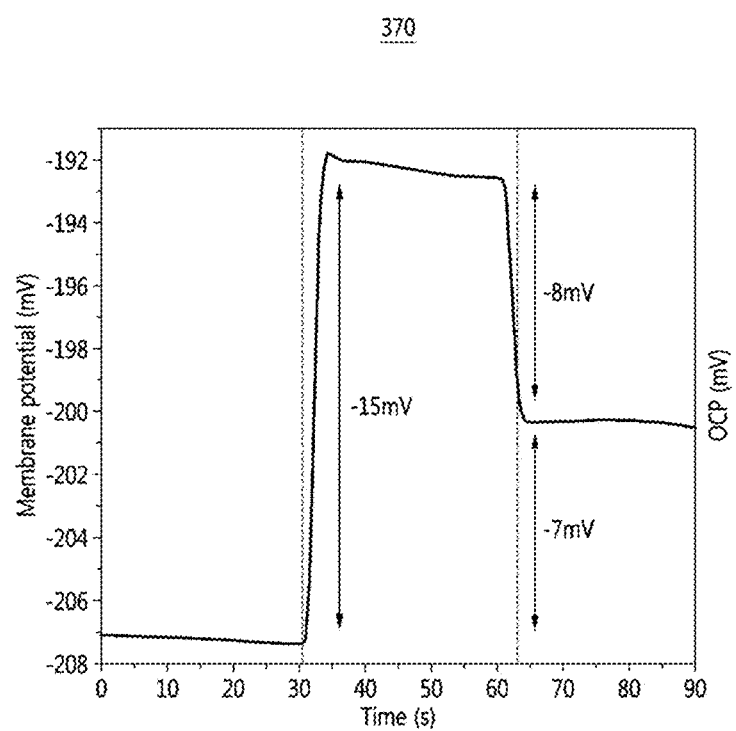

Hereinafter, the embodiments of the present disclosure will be described in detail with reference to the drawings.

However, it should be understood that the present disclosure is not limited to the embodiments according to the concept of the present disclosure, but includes changes, equivalents, or alternatives falling within the spirit and scope of the present disclosure.

In the following description of the present disclosure, detailed description of known functions and configurations incorporated herein will be omitted when it may make the subject matter of the present disclosure unclear.

In addition, the terms used in the specification are defined in consideration of functions used in the present disclosure, and can be changed according to the intent or conventionally used methods of clients, operators, and users. Accordingly, definitions of the terms should be understood on the basis of the entire description of the present specification.

In description of the drawings, like reference numerals may be used for similar elements.

The singular expressions in the present specification may encompass plural expressions unless clearly specified otherwise in context.

In this specification, expressions such as "A or B" and "at least one of A and/or B" may include all possible combinations of the items listed together.

Expressions such as "first" and "second" may be used to qualify the elements irrespective of order or importance, and are used to distinguish one element from another and do not limit the elements.

It will be understood that when an element (e.g., first) is referred to as being "connected to" or "coupled to" another element (e.g., second), it may be directly connected or coupled to the other element or an intervening element (e.g., third) may be present.

As used herein, "configured to" may be used interchangeably with, for example, "suitable for", "ability to", "changed to", "made to", "capable of", or "designed to" in terms of hardware or software.

In some situations, the expression "device configured to" may mean that the device "may do~" with other devices or components.

For example, in the sentence "processor configured to perform A, B, and C", the processor may refer to a general purpose processor (e.g., CPU or application processor) capable of performing corresponding operation by running a dedicated processor (e.g., embedded processor) for performing the corresponding operation, or one or more software programs stored in a memory device.

In addition, the expression "or" means "inclusive or" rather than "exclusive or".

That is, unless mentioned otherwise or clearly inferred from context, the expression "x uses a or b" means any one of natural inclusive permutations.

In the above-described specific embodiments, elements included in the invention are expressed in singular or plural in accordance with the specific embodiments shown.

It should be understood, however, that the singular or plural representations are to be chosen as appropriate to the situation presented for the purpose of description and that the above-described embodiments are not limited to the singular or plural constituent elements. The constituent elements expressed in plural may be composed of a single number, and constituent elements expressed in singular form may be composed of a plurality of elements.

In addition, the present disclosure has been described with reference to exemplary embodiments, but it should be understood that various modifications may be made without departing from the scope of the present disclosure.

Therefore, the scope of the present disclosure should not be limited by the embodiments, but should be determined by the following claims and equivalents to the following claims.

FIG. 1 illustrates an integrated biochemical sensor according to one embodiment.

Referring to FIG. 1, an integrated biochemical sensor 100 according to one embodiment may simultaneously detect a plurality of biochemical substances using a reference electrode and a plurality of working electrodes having different types of artificial lipid membranes.

In addition, in the integrated biochemical sensor 100, a plurality of working electrodes is designed to have a laminated structure consisting of a stabilizing layer, an electrolyte layer, and an artificial lipid membrane. Thus, in detecting a signal corresponding to a biochemical substance, reliability and stability may be increased, and sustainability for sensing operation may be secured.

The integrated biochemical sensor 100 may include a reference electrode RE, a plurality of working electrodes WE1 to WE4, and partition layers W.

The working electrodes WE1 to WE4 according to one embodiment may include artificial lipid membranes. For example, the working electrodes WE1 to WE4 may each include artificial lipid membranes formed of different materials, and thus the integrated biochemical sensor 100 may simultaneously detect a plurality of biochemical substances.

In addition, the partition layers W according to one embodiment may electrically insulate the reference electrode RE and each of the working electrodes WE1 to WE4.

Specifically, the reference electrode RE may be disposed in the central region of the integrated biochemical sensor 100, and the working electrodes WE1 to WE4 for detecting or measuring a plurality of biochemical ions may be disposed in a plurality of regions corresponding to the outer circumferential surface of the reference electrode RE.

In addition, artificial lipid membranes for selectively measuring respective biochemical ions may be disposed on the tops of the working electrodes WE1 to WE4, respectively, and the artificial lipid membranes may be separated from each other and electrically insulated from each other by the partition layers W.

Hereinafter, the integrated biochemical sensor 100 including four working electrodes WE1 to WE4 will be described as an example. However, the integrated biochemical sensor 100 according to one embodiment is not limited thereto, and may include two or three working electrodes or five or more working electrodes.

According to one aspect, the membrane potential of the artificial lipid membranes may be changed due to chemical reaction between the artificial lipid membranes and biochemical ions.

In addition, the integrated biochemical sensor 100 may detect biochemical ions based on the potential difference between the reference electrode RE and a working electrode having an artificial lipid membrane, the membrane potential of which is changed, among the working electrodes WE1 to WE4.

That is, when a potential difference between the reference electrode RE and a working electrode including an artificial lipid membrane, the membrane potential of which is changed due to detection of biochemical ions (biochemical substances), is generated, the integrated biochemical sensor 100 may determine whether biochemical ions have been detected based on the generated potential difference. For this function, the integrated biochemical sensor 100 may further include a detection judgment device.

In addition, without determining whether biochemical substances have been detected, the integrated biochemical sensor 100 may transmit information about the potential difference between the reference electrode RE and a working electrode including an artificial lipid membrane, the membrane potential of which is changed, to a detection judgment device separately provided outside.

According to one aspect, each of the working electrodes WE1 to WE4 may further include a working electrode layer, a stabilizing layer, and an electrolyte layer for improving electrical connectivity between the working electrode layer and the artificial lipid membrane. Preferably, each of the working electrodes WE1 to WE4 may be formed to have a laminated structure in which the working electrode layer, the stabilizing layer, the electrolyte layer, and the artificial lipid membrane are laminated.

For example, the working electrode layer may include at least one of chromium (Cr) and gold (Au).

In addition, the stabilizing layer may include at least one of silver (Ag), silver chloride (AgCl), and polyvinyl butyral (PVB). Preferably, the stabilizing layer includes silver (Ag) and silver chloride (AgCl), i.e., Ag/AgCl.

Specifically, Ag/AgCl is a very chemically stable material. A conventional aqueous silver solution has a problem in that current changes severely depending on the amount of ions in the solution. When using Ag/AgCl, this problem may be solved.

In addition, the electrolyte layer may include at least one of poly(2-hydroxyethyl methacrylate) (pHEMA) and PEDOT:PSS.

The working electrodes WE1 to WE4 may include the first working electrode WE1 for detecting biochemical ions corresponding to saltiness through a first artificial lipid membrane, the second working electrode WE2 for detecting biochemical ions corresponding to bitterness through a second artificial lipid membrane, the third working electrode WE3 for detecting biochemical ions corresponding to sweetness through a third artificial lipid membrane, and the fourth working electrode WE4 for detecting biochemical ions corresponding to sourness through a fourth artificial lipid membrane.

That is, the integrated biochemical sensor 100 may be implemented as a taste sensor for detecting saltiness, bitterness, sweetness, and sourness, without being limited thereto.

Specifically, the first artificial lipid membrane may include at least one of tetradodecylammonium, bromide 1-hexadecanol, and di-n-octyl phenylphosphonate. Preferably, the first artificial lipid membrane is formed of a mixture of tetradodecylammonium, bromide 1-hexadecanol, and di-n-octyl phenylphosphonate.

In addition, the second artificial lipid membrane may include at least one of methyl trioctyl ammonium chloride and di-n-octyl phenylphosphonate. Preferably, the second artificial lipid membrane is formed of a mixture of methyl trioctyl ammonium chloride and di-n-octyl phenylphosphonate.

In addition, the third artificial lipid membrane may include at least one of tetradodecylammonium bromide and di-n-octyl phenylphosphonate. Preferably, the third artificial lipid membrane is formed of a mixture of tetradodecylammonium bromide and di-n-octyl phenylphosphonate.

In addition, the fourth artificial lipid membrane may include at least one of methyl trioctyl ammonium chloride, oleic acid, bis(2-ethylhexyl) phosphate, and dioctyl phenyl phosphonate. Preferably, the fourth artificial lipid membrane is formed of a mixture of methyl trioctyl ammonium chloride, oleic acid, bis(2-ethylhexyl) phosphate, and dioctyl phenyl phosphonate.

According to one aspect, the partition layers W may include a lower encapsulation layer for protecting the working electrodes WE1 to WE4 from external impact and damage and electrically insulating the working electrodes WE1 to WE4, an insulating encapsulation layer for electrically insulating each of the working electrodes WE1 to WE4 and the reference electrode RE, and an upper encapsulation layer for protecting the reference electrode RE from external impact and damage and electrically insulating the reference electrode RE.

Preferably, the lower encapsulation layer, the insulating encapsulation layer, and the upper encapsulation layer may include parylenes.

In addition, the integrated biochemical sensor 100 may further include a wireless communication device for transmitting signals (e.g., voltage values) measured through the reference electrode RE and the working electrodes WE1 to WE4 to the outside and wiring for connecting the reference electrode RE and each of the working electrodes WE1 to WE4 to the wireless communication device.

In addition, the reference electrode RE, the working electrodes WE1 to WE4, the wiring, and the wireless communication device may be mounted on a stretchable substrate.

For example, the substrate may be a film based on at least one of a polyimide film and a polyethylene terephthalate (PET) film.

In addition, the wiring may include a plurality of electrode patterns that connect the reference electrode RE and each of the working electrodes WE1 to WE4 to the wireless communication device. The electrode patterns may be implemented as meander patterns having a serpentine shape to cover a relatively large area.

In addition, the wireless communication device may include a detection judgment device that determines whether biochemical substances are detected based on a potential difference deduced through voltage values from the reference electrode RE and each of the working electrodes WE1 to WE4 through the electrode patterns, and that outputs a detection signal based on the judgment result.

In addition, the wireless communication device may further include a differential amplifier for amplifying the output signal, a low-pass filter for filtering out a noise signal from the amplified detection signal, and a wireless output device for outputting, to the outside through wireless communication, the detection signal from which the noise signal has been filtered out.

For example, the wireless output device may output signals to at least one wireless communication means of ZigBee, Bluetooth, Z-Wave, Wi-Fi, Wi-Max, IEEE 802.11, and Shared Wireless Access Protocol (SWAP) according to coverage.

FIGS. 2A to 2E are diagrams for explaining the process of detecting biochemical ions using an integrated biochemical sensor according to one embodiment.

Referring to FIGS. 2A to 2E, reference numeral 200 shows a timing diagram of a process of detecting and stabilizing biochemical ions performed by the integrated biochemical sensor according to one embodiment.

In addition, reference numerals 210 to 240 illustrate chemical reactions occurring in the integrated biochemical sensor according to execution of detailed processes shown in the timing diagram of reference numeral 200.

Specifically, reference numeral 210 illustrates a process of immersing the integrated biochemical sensor in a reference solution, and reference numeral 220 illustrates a sensing process of reacting the integrated biochemical sensor with a reaction solution including a biochemical substance.

In addition, reference numeral 230 illustrates a first stabilization process in which the integrated biochemical sensor is once again immersed in the reference solution, and reference numeral 240 illustrates a second stabilization process in which the integrated biochemical sensor is immersed in a washing solution containing an ethanol component.

For example, the reference solution may be a solution prepared by mixing 30 mM potassium chloride (KCl) and 0.3 mM tartaric acid.

According to reference numerals 210 to 220, the integrated biochemical sensor may detect biochemical ions through a two-electrode measurement method of measuring the potential difference between the reference electrode and the working electrode.

Specifically, when the reference electrode and the working electrode including an artificial lipid membrane are immersed in a solution (reference solution), an electrical double layer may be formed on the surface of the artificial lipid membrane, i.e., polarity may be formed on the surface of the artificial lipid membrane.

Next, when the working electrode and the reference electrode are immersed in a sample solution containing a biochemical substance while an electrical double layer is formed on the artificial lipid membrane, the sample solution is ionized in an aqueous solution, and charged ions (biochemical ions) react with the artificial lipid membrane, changing the potential difference ($V_s$-$V_f$) between the working electrode and the reference electrode.

For example, the biochemical ions may be ions corresponding to at least one of sweetness, bitterness, sourness, saltiness, astringency, and savory taste.

The detection process of the integrated biochemical sensor according to one embodiment will be described in more detail with reference to FIGS. 3A to 3G.

According to reference numerals 230 and 240, when the working electrode and the reference electrode used in the detection process are immersed in the reference solution again and washed (first stabilization process), the sample solution may be removed from the surface of the artificial lipid membrane. At this time, voltage may decrease to a CPA value ($V_f$-$V_f$).

Next, when the working electrode and the reference electrode are washed once again with a washing solution containing an ethanol component to remove the sample solution adsorbed in the artificial lipid membrane and are subjected to a second stabilization process in the reference solution, the artificial lipid membrane may be changed to the initial potential level.

That is, the artificial lipid membrane of the integrated biochemical sensor according to one embodiment may be restored to the original state thereof through the stabilization process described above, and thus the integrated biochemical sensor may be reused repeatedly.

FIGS. 3A to 3G are diagrams for explaining examples of detecting biochemical ions corresponding to sourness and bitterness using an integrated biochemical sensor according to one embodiment.

Referring to FIGS. 3A to 3G, reference numeral 310 illustrates chemical reaction occurring in an artificial lipid membrane in an aqueous solution (reference solution), reference numeral 320 illustrates chemical reaction occurring in an artificial lipid membrane in a hydrochloric acid (HCl) solution corresponding to sourness, reference numeral 330 illustrates chemical reaction occurring in an artificial lipid membrane in a sodium chloride (NaCl) solution corresponding to bitterness, and reference numeral 340 illustrates chemical reaction occurring in an artificial lipid membrane in a quinine solution corresponding to bitterness.

In addition, reference numeral 350 illustrates the sourness test results of the integrated biochemical sensor according to one embodiment, reference numeral 360 illustrates the saltiness test results of the integrated biochemical sensor, and reference numeral 370 illustrates the bitterness test results of the integrated biochemical sensor.

According to reference numeral 310, when the integrated biochemical sensor including the artificial lipid membrane is immersed in the aqueous solution (reference solution), as acid radicals are dissociated from the artificial lipid membrane, an electrical double layer is formed around the artificial lipid membrane, thereby forming a membrane potential ($V_m$).

According to reference numerals 320 and 350, biochemical ions corresponding to sourness cause change in the membrane potential ($\Delta V_m$) of the artificial lipid membrane by preventing the dissociation phenomenon in the artificial lipid membrane, the membrane potential changes according to change in the concentration of sourness. Specifically, as the concentration of sourness increases, the magnitude of an open circuit potential (OCP) in the integrated biochemical sensor increases significantly.

According to reference numeral 330, biochemical ions ($Na^+$) corresponding to bitterness may change the membrane potential of the artificial lipid membrane by forming an electrical double layer around the artificial lipid membrane.

According to reference numeral 340, as biochemical ions ($Q^-$) corresponding to bitterness are adsorbed onto the artificial lipid membrane, the membrane potential of the artificial lipid membrane may be changed.

According to reference numeral 370, as described above, an electrical double layer is formed around the artificial lipid membrane by biochemical ions corresponding to bitterness or biochemical ions corresponding to bitterness are adsorbed onto the artificial lipid membrane, thereby changing an open circuit potential (OCP).

In addition, biochemical ions corresponding to sweetness and biochemical ions corresponding to saltiness may be detected through the same manner as the method of detecting sourness.

According to reference numeral 360, as in the case of sourness, as the concentration of biochemical ions corresponding to saltiness increases, voltage increases.

That is, the integrated biochemical sensor according to one embodiment may measure a potential difference for each concentration of biochemical ions through the above-described method, or may measure a plurality of biochemical ions at once.

Figure 4:
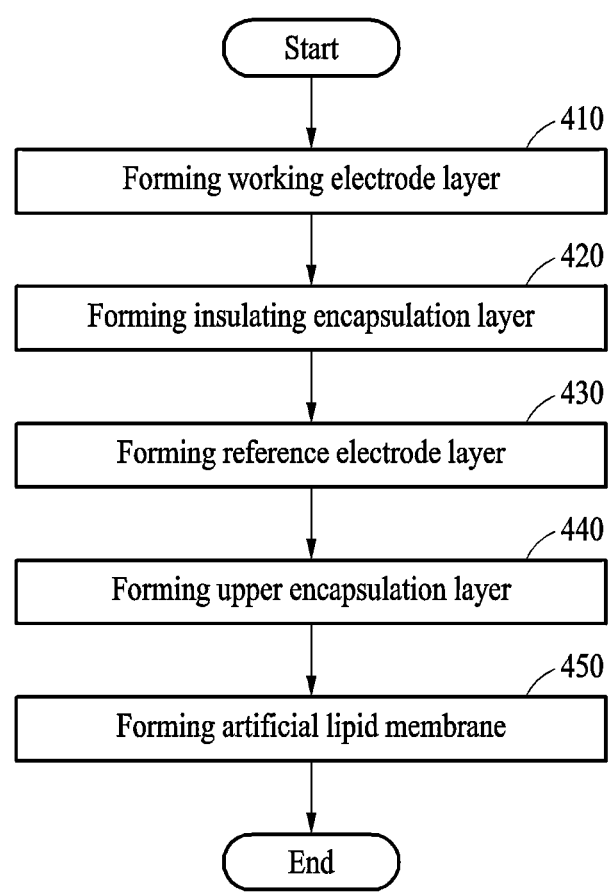
FIG. 4 is a flowchart for explaining a method of manufacturing an integrated biochemical sensor according to one embodiment.

FIG. 4 is a flowchart for explaining a method of manufacturing an integrated biochemical sensor according to one embodiment.

That is, FIG. 4 is a flowchart for explaining a method of manufacturing the integrated biochemical sensor according to one embodiment described with reference to FIGS. 1 to 3G. When describing FIG. 4, descriptions overlapping with those described with reference to FIGS. 1 to 3G will be omitted.

Referring to FIG. 4, according to the method of manufacturing an integrated biochemical sensor according to one embodiment, in step 410, a plurality of working electrode layers may be formed.

Next, according to the method of manufacturing an integrated biochemical sensor according to one embodiment, in step 420, an insulating encapsulation layer for electrically insulating each of the working electrode layers and a reference electrode layer may be formed.

Next, according to the method of manufacturing an integrated biochemical sensor according to one embodiment, in step 430, the reference electrode layer may be formed on the insulating encapsulation layer.

Next, according to the method of manufacturing an integrated biochemical sensor according to one embodiment, in step 430, artificial lipid membranes may be formed on the working electrode layers, respectively.

The method of manufacturing an integrated biochemical sensor according to one embodiment will be described in more detail with reference to FIGS. 5 to 6D.

Figure 5:
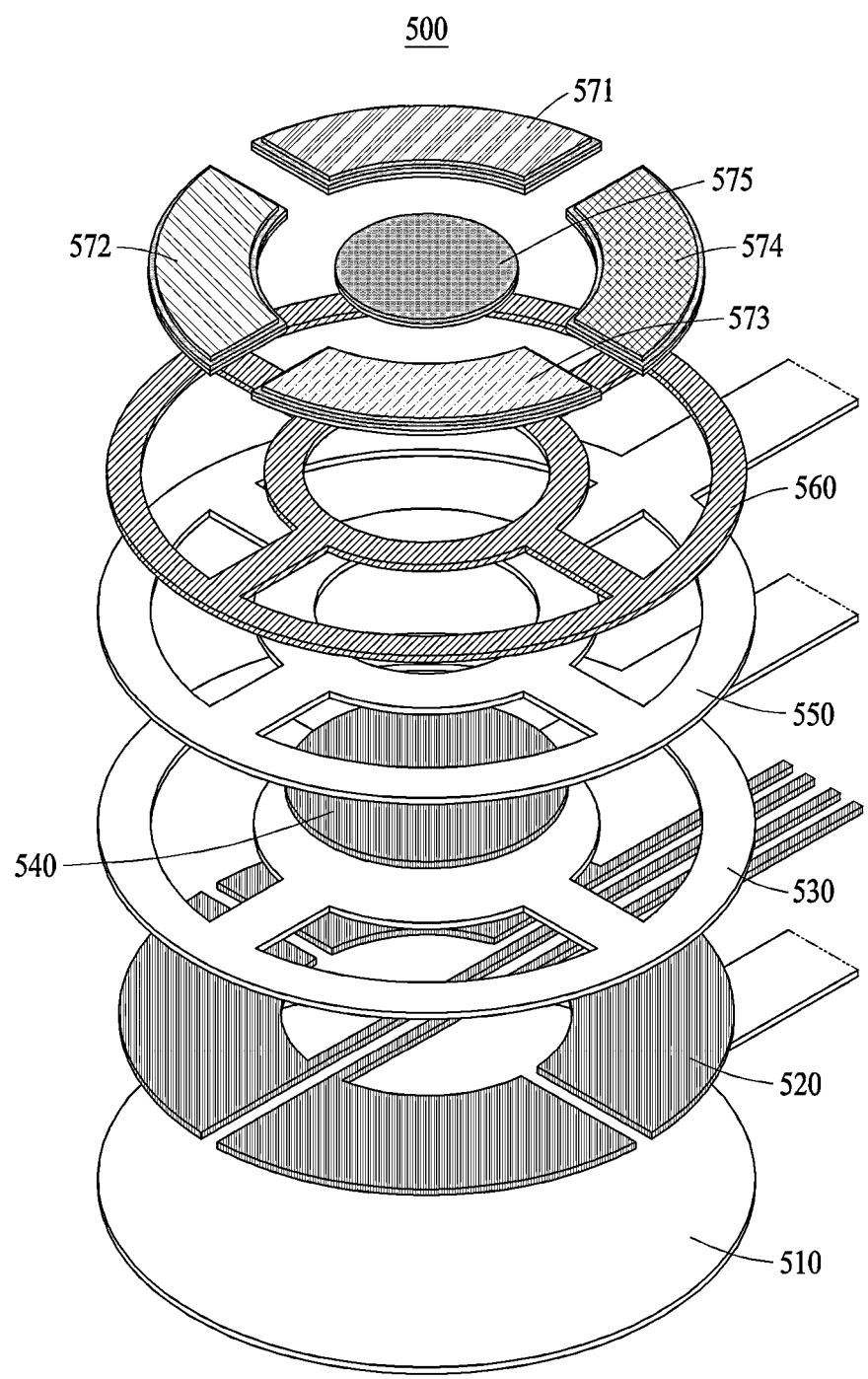
FIG. 5 is a drawing for explaining in more detail a method of manufacturing an integrated biochemical sensor according to one embodiment.
Figure 6A:
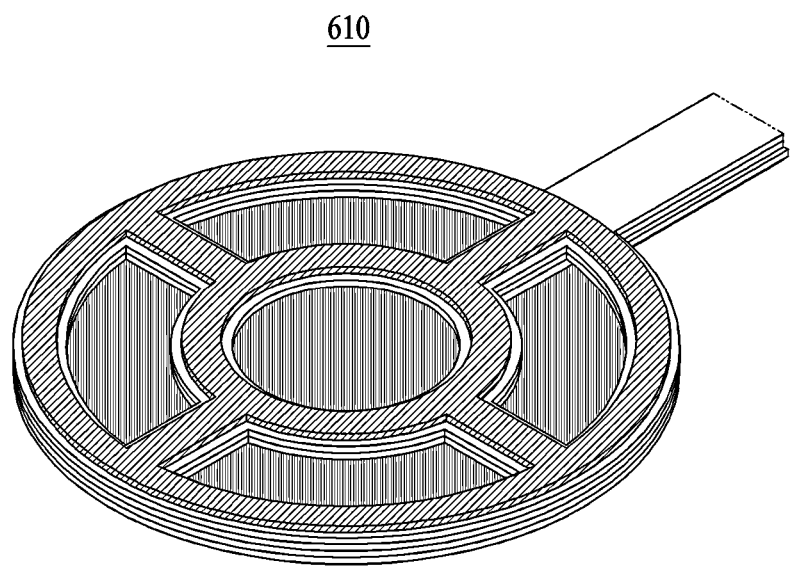
FIGS. 6A to 6D are drawings for explaining in more detail a step of forming artificial lipid membranes in a method of manufacturing an integrated biochemical sensor according to one embodiment.
Figure 6B:
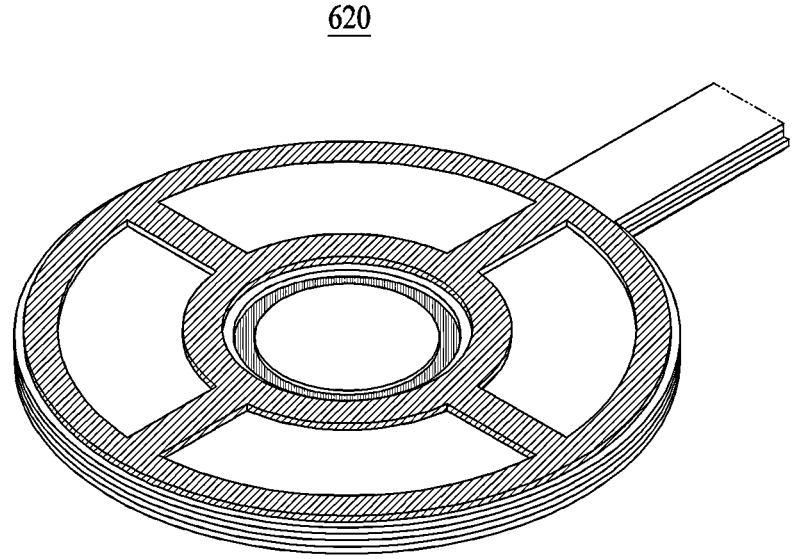
Figure 6C:
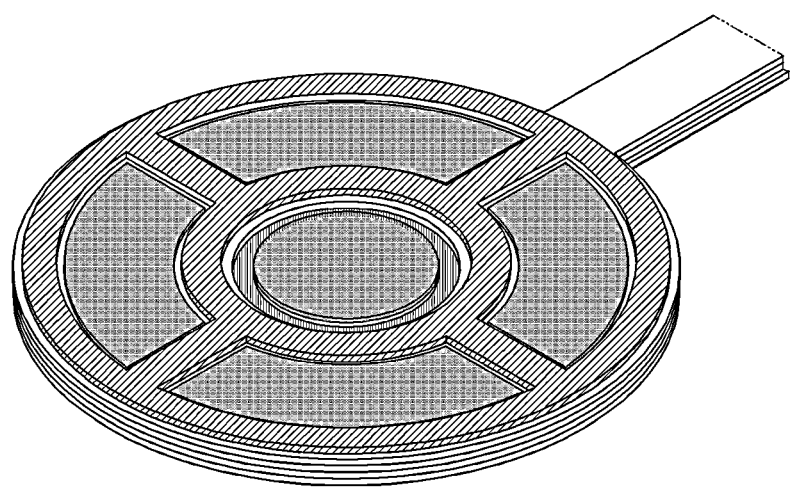
Figure 6D:
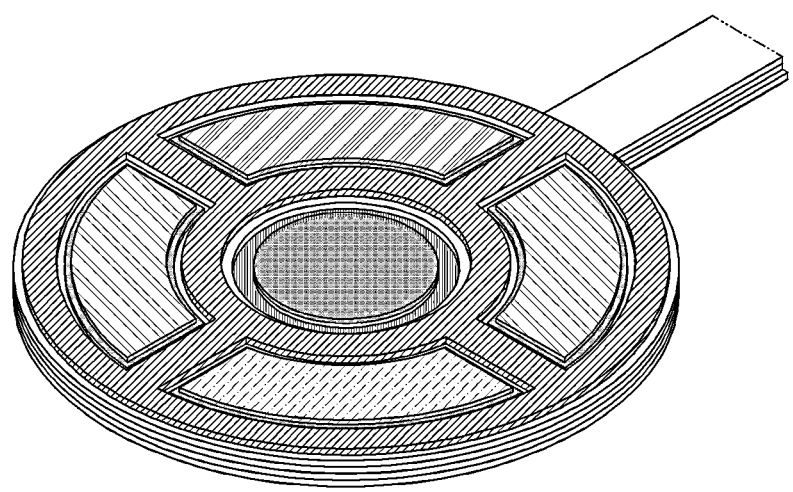

FIG. 5 is a drawing for explaining in more detail a method of manufacturing an integrated biochemical sensor according to one embodiment.

Referring to FIG. 5, according to the method of manufacturing an integrated biochemical sensor according to one embodiment, a lower encapsulation layer 510 for preventing a plurality of working electrode layers 520 from external impact and damage and electrically insulating the working electrode layers 520 may be formed on a dielectric layer.

Next, according to the method of manufacturing an integrated biochemical sensor according to one embodiment, an insulating encapsulation layer 530 for electrically insulating each of the working electrode layers 520 and a reference electrode layer 540 may be formed on the working electrode layers 520.

Next, according to the method of manufacturing an integrated biochemical sensor according to one embodiment, an upper encapsulation layer 550 for preventing the reference electrode layer 540 from external impact and damage and electrically insulating the reference electrode layer 540 may be formed on the insulating encapsulation layer 530.

Next, according to the method of manufacturing an integrated biochemical sensor according to one embodiment, a partition structure 560 may be formed on the upper encapsulation layer 550.

Next, according to the method of manufacturing an integrated biochemical sensor according to one embodiment, a stabilizing layer/an electrolyte layer/an artificial lipid membrane 571 to 574 may be formed on each of the working electrode layers 520, and a stabilizing layer/an electrolyte layer 575 may be formed on the reference electrode layer 540.

FIGS. 6A to 6D are drawings for explaining in more detail a step of forming artificial lipid membranes in a method of manufacturing an integrated biochemical sensor according to one embodiment.

That is, the manufacturing method described with reference to FIGS. 6A to 6D may be performed in step 450 of FIG. 4.

Referring to FIGS. 6A to 6D, according to the method of manufacturing an integrated biochemical sensor according to one embodiment, in step 610, a structure in which each of a plurality of working electrode layers and a reference electrode layer are electrically insulated by partition layers may be formed. That is, the electrically insulated structure may be a structure formed through steps 410 to 440 of FIG. 4.

Next, according to the method of manufacturing an integrated biochemical sensor according to one embodiment, in step 620, a stabilizing layer may be formed on the working electrode layers and the reference electrode layer. Preferably, the stabilizing layer includes silver (Ag) and silver chloride (AgCl), (i.e., Ag/AgCl).

Next, according to the method of manufacturing an integrated biochemical sensor according to one embodiment, in step 630, an electrolyte layer may be formed on the working electrode layers on which the stabilizing layer has been formed and the reference electrode layer on which the stabilizing layer has been formed. Preferably, the electrolyte layer includes poly(2-hydroxyethyl methacrylate) (pHEMA).

Specifically, according to the method of manufacturing an integrated biochemical sensor according to one embodiment, in step 630, an electrolyte layer may be formed by performing polymerization by selectively dropping an electrolyte material on the working electrode layers and the reference electrode layer on which the Ag/AgCl dough has been formed.

Next, according to the method of manufacturing an integrated biochemical sensor according to one embodiment, in step 640, artificial lipid membranes may be formed on the working electrode layers on which the electrolyte layer has been formed.

Specifically, according to the method of manufacturing an integrated biochemical sensor according to one embodiment, in step 640, different artificial lipid membranes may be formed on the working electrode layers on which the electrolyte layer has been formed. In this case, different electrodes may not influence each other due to the partition layers.

In summary, when the present disclosure is used, a plurality of biochemical substances may be simultaneously detected using a reference electrode and a plurality of working electrodes having different artificial lipid membranes.

In addition, a plurality of working electrodes is designed to have a laminated structure consisting of a stabilizing layer, an electrolyte layer, and an artificial lipid membrane. Thus, in detecting a signal corresponding to a biochemical substance, reliability and stability may be increased, and sustainability for sensing operation may be secured.

According to one embodiment of the present disclosure, a plurality of biochemical substances can be simultaneously detected using a reference electrode and a plurality of working electrodes having different types of artificial lipid membranes.

In addition, a plurality of working electrodes is designed to have a laminated structure consisting of a stabilizing layer, an electrolyte layer, and an artificial lipid membrane. Thus, in detecting a signal corresponding to a biochemical substance, reliability and stability can be increased, and sustainability for sensing operation can be secured.

Although the present disclosure has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

DESCRIPTION OF SYMBOLS

100: INTEGRATED BIOCHEMICAL SENSOR
RE: REFERENCE ELECTRODE
WE1: FIRST WORKING ELECTRODE
WE2: SECOND WORKING ELECTRODE
WE3: THIRD WORKING ELECTRODE
WE4: FOURTH WORKING ELECTRODE
W: PARTITION LAYERS

What is claimed is:

1. An integrated biochemical sensor, comprising:
a plurality of working electrode layers;
an insulating encapsulation layer including a central portion and a plurality of first openings on the working electrode layers, the first openings being along a periphery of the central portion and corresponding to the working electrode layers, respectively, the insulating encapsulation layer configured to electrically insulate each of the working electrode layers and a reference electrode layer;
the reference electrode layer on the central portion of the insulating encapsulation layer;
a partition structure including a plurality of second openings on the insulating encapsulation layer and electrically insulating the reference electrode layer and the working electrode layers from each other, the partition structure exposing the reference electrode layer and the working electrode layers through the second openings;
a plurality of working electrode structures each having different artificial lipid membranes and being on the working electrode layers, respectively; and
a reference electrode structure on the reference electrode layer,
wherein a reference electrode comprising the reference electrode layer and the reference electrode structure is in a central region, and
wherein working electrodes comprising respective pairs of the working electrode layers and the plurality of working electrode structures are in a plurality of regions around an outer circumferential surface of the reference electrode, respectively.

2. The integrated biochemical sensor according to claim 1, wherein membrane potentials of the artificial lipid membranes change due to chemical reaction with biochemical ions corresponding to the artificial lipid membranes.

3. The integrated biochemical sensor according to claim 2, wherein the biochemical ions are detected based on a potential difference between the reference electrode and respective one of the working electrodes.

4. The integrated biochemical sensor according to claim 1, wherein each of the working electrodes further comprises a corresponding one of the working electrode layer, a stabilizing layer, and an electrolyte layer for improving electrical connectivity between the corresponding one of the working electrode layers and a corresponding one of the artificial lipid membranes.

5. The integrated biochemical sensor according to claim 4, wherein the stabilizing layer comprises at least one of silver (Ag), silver chloride (AgCl), and polyvinyl butyral (PVB).

6. The integrated biochemical sensor according to claim 4, wherein the electrolyte layer comprises at least one of poly(2-hydroxyethyl methacrylate) (pHEMA) and Poly(3,4-ethylenedioxythiophene):poly(styrenesulfonate) PEDOT:PSS).

7. The integrated biochemical sensor according to claim 1, further comprising:
a lower encapsulation layer for protecting the working electrodes from external impact under the working electrode layers,
the insulating encapsulation layer for electrically insulating each of the working electrodes and the reference electrode on the working electrode layers, and
an upper encapsulation layer for protecting the reference electrode from external impact on the insulating encapsulation layer and under the partition structure.

8. The integrated biochemical sensor according to claim 1, wherein
the artificial lipid membranes include a first artificial lipid membrane, a second artificial lipid membrane, a third artificial lipid membrane, and a fourth artificial lipid membrane, and
the working electrodes comprise a first working electrode for detecting biochemical ions corresponding to saltiness through the first artificial lipid membrane, a second working electrode for detecting biochemical ions corresponding to bitterness through the second artificial lipid membrane, a third working electrode for detecting biochemical ions corresponding to sweetness through the third artificial lipid membrane, and a fourth working electrode for detecting biochemical ions corresponding to sourness through the fourth artificial lipid membrane.

9. The integrated biochemical sensor according to claim 8, wherein the first artificial lipid membrane comprises at least one of tetradodecylammonium, bromide 1-hexadecanol, and di-n-octyl phenylphosphonate.

10. The integrated biochemical sensor according to claim 8, wherein the second artificial lipid membrane comprises at least one of methyl trioctyl ammonium chloride and di-n-octyl phenylphosphonate.

11. The integrated biochemical sensor according to claim 8, wherein the third artificial lipid membrane comprises at least one of tetradodecylammonium bromide and di-n-octyl phenylphosphonate.

12. The integrated biochemical sensor according to claim 8, wherein the fourth artificial lipid membrane comprises at least one of methyl trioctyl ammonium chloride, oleic acid, bis(2-ethylhexyl) phosphate, and dioctyl phenyl phosphonate.

13. A method of manufacturing an integrated biochemical sensor, comprising:
   forming a plurality of working electrode layers;
   forming an insulating encapsulation layer including a central portion and a plurality of first openings on the working electrode layers, the first openings being along a periphery of the central portion and corresponding to the working electrode layers, respectively, such that the insulating encapsulation layer electrically insulates each of the working electrode layers and a reference electrode layer;
   forming the reference electrode layer on the central portion of the insulating encapsulation layer;
   forming an upper encapsulation layer on the insulating encapsulation layer for protecting the reference electrode layer from external impact on the insulating encapsulation layer;
   forming a partition structure including a plurality of second openings on the insulating encapsulation layer on the upper encapsulation layer such that the partition structure electrically insulates the reference electrode layer and the working electrode layers from each other, and exposes the reference electrode layer and the working electrode layers through the second openings; and
   forming artificial lipid membranes on the working electrode layers,
   wherein the reference electrode layer is in a central region, and
   wherein the working electrode layers are in a plurality of regions around an outer circumferential surface of the reference electrode layer, respectively.

14. The method according to claim 13, wherein the forming of the artificial lipid membranes comprises:
   forming a stabilizing layer on the working electrode layers and the reference electrode layer;
   forming an electrolyte layer on the working electrode layers on which the stabilizing layer has been formed and the reference electrode layer on which the stabilizing layer has been formed; and
   forming the artificial lipid membranes on the working electrode layers on which the electrolyte layer has been formed.

\* \* \* \* \*